United States Patent
Hatanaka et al.

(10) Patent No.: US 9,526,675 B2
(45) Date of Patent: Dec. 27, 2016

(54) DENTINAL TUBULE SEALING MATERIAL

(71) Applicant: KURARAY NORITAKE DENTAL INC., Kurashiki-shi (JP)

(72) Inventors: Kenji Hatanaka, Niigata (JP); Shumei Ishihara, Niigata (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 14/909,803

(22) PCT Filed: Aug. 4, 2014

(86) PCT No.: PCT/JP2014/004077
§ 371 (c)(1),
(2) Date: Feb. 3, 2016

(87) PCT Pub. No.: WO2015/019601
PCT Pub. Date: Feb. 12, 2015

(65) Prior Publication Data
US 2016/0193118 A1    Jul. 7, 2016

(30) Foreign Application Priority Data
Aug. 6, 2013  (JP) ................. 2013-163390

(51) Int. Cl.
*A61K 6/00* (2006.01)
*A61K 8/24* (2006.01)
*A61Q 11/00* (2006.01)
*A61K 8/19* (2006.01)
*A61K 8/02* (2006.01)

(52) U.S. Cl.
CPC ............ *A61K 6/007* (2013.01); *A61K 6/0008* (2013.01); *A61K 6/0038* (2013.01); *A61K 6/0082* (2013.01); *A61K 8/0241* (2013.01); *A61K 8/19* (2013.01); *A61K 8/24* (2013.01); *A61Q 11/00* (2013.01)

(58) Field of Classification Search
CPC ............ A61K 6/007; A61K 8/24; A61K 8/19; A61K 6/0008; A61K 6/0038; A61K 6/0082; A61K 8/0241; A61Q 11/00
See application file for complete search history.

(56) References Cited

U.S. PATENT DOCUMENTS

| | | | |
|---|---|---|---|
| 2012/0027829 A1* | 2/2012 | Hashimoto | A61K 6/0017 424/401 |
| 2013/0189337 A1* | 7/2013 | Hashimoto | A61K 6/0017 424/401 |
| 2013/0251767 A1 | 9/2013 | Hashimoto et al. | |

FOREIGN PATENT DOCUMENTS

| | | | | |
|---|---|---|---|---|
| JP | WO2012/046667 | * | 4/2012 | ............. A61K 6/033 |
| WO | 2010/113800 A1 | | 10/2010 | |
| WO | 2010/113801 A1 | | 10/2010 | |
| WO | 2012/046667 A1 | | 4/2012 | |

OTHER PUBLICATIONS

Isabel Porto, et al, Diagnosis and Treatment of Dentinal Hypersensitivity, 51 J Oral Sci. 323 (2009).*
International Search Report issued Oct. 14, 2014 in PCT/JP2014/004077 filed Aug. 4, 2014.

* cited by examiner

*Primary Examiner* — Sean Basquill
(74) *Attorney, Agent, or Firm* — Oblon, McClelland, Maier & Neustadt, L.L.P.

(57) ABSTRACT

The present invention provides a dentinal tubule sealing material excellent in durability of dentinal tubule sealing performance (acid resistance) and also in storage stability. The present invention relates to a dentinal tubule sealing material including tetracalcium phosphate particles (A), calcium hydrogen phosphate particles (B), calcium carbonate particles (C), and a non-aqueous dispersant (D), the dentinal tubule sealing material including 5 to 75 parts by weight of the tetracalcium phosphate particles (A), 10 to 70 parts by weight of the calcium hydrogen phosphate particles (B), and 2 to 50 parts by weight of the calcium carbonate particles (C) per 100 parts by weight of the total of the tetracalcium phosphate particles (A), the calcium hydrogen phosphate particles (B), and the calcium carbonate particles (C).

20 Claims, No Drawings

DENTINAL TUBULE SEALING MATERIAL

TECHNICAL FIELD

The present invention relates to a dentinal tubule sealing material excellent in durability of dentinal tubule sealing performance and also in storage stability.

BACKGROUND ART

Inhibition of pain associated with dentin exposure is a clinical challenge. Examples of the cause of dentin exposure include gingival recession, wedge-shaped defect, abutment tooth preparation, and cavity formation. Although the mechanism of occurrence of pain has not been fully defined yet, there has been known the hydrodynamic theory stating that external sensation causes the movement of the internal fluid in dentinal tubules, thereby stimulating pulp nerves. For inhibition of pain, it is considered effective to control the movement of the internal fluid in dentinal tubules by sealing the dentinal tubules.

An example of means for sealing dentinal tubules is a dentinal tubule sealing material described in Patent Literature 1, which material contains poorly-soluble calcium phosphate particles and a phosphorus-free calcium compound. According to this literature, it has been confirmed that when the sealing material obtained as a paste is rubbed on dentin with a microbrush for 30 seconds, dentinal tubules can be sealed with the sealing material, and a high dentin penetration inhibition ratio can be achieved. However, the dentinal tubule sealing material described in Patent Literature 1 has room for improvement in terms of its storage stability and the durability of the resulting sealing product.

Patent Literature 2 describes a dentin mineralizing agent including tetracalcium phosphate particles, an alkali metal phosphate, and acid calcium phosphate particles, and proposes a method including applying the agent obtained as a paste to dentin surface. This method enables sealing of a large proportion of dentinal tubules, and can therefore be expected to effectively inhibit pain. However, the dentin mineralizing agent described in Patent Literature 2 has room for improvement in terms of its storage stability and the durability of the resulting sealing product.

CITATION LIST

Patent Literature

Patent Literature 1: WO 2012/046667 A1
Patent Literature 2: WO 2010/113800 A1

SUMMARY OF INVENTION

Technical Problem

The present invention aims to provide a dentinal tubule sealing material excellent in durability of dentinal tubule sealing performance and also in storage stability.

Solution to Problem

The present invention is a dentinal tubule sealing material including tetracalcium phosphate particles (A), calcium hydrogen phosphate particles (B), calcium carbonate particles (C), and a non-aqueous dispersant (D), the dentinal tubule sealing material including 5 to 75 parts by weight of the tetracalcium phosphate particles (A), 10 to 70 parts by weight of the calcium hydrogen phosphate particles (B), and 2 to 50 parts by weight of the calcium carbonate particles (C) per 100 parts by weight of the total of the tetracalcium phosphate particles (A), the calcium hydrogen phosphate particles (B), and the calcium carbonate particles (C).

In the dentinal tubule sealing material of the present invention, it is preferable that the tetracalcium phosphate particles (A) have an average particle diameter of 0.5 to 10 µm, the calcium hydrogen phosphate particles (B) have an average particle diameter of 0.1 to 7.5 µm, and the calcium carbonate particles (C) have an average particle diameter of 0.1 to 12 µm.

The dentinal tubule sealing material of the present invention preferably further includes 0.1 to 100 parts by weight of silica and/or metal oxide particles (E) having an average particle diameter of 0.002 to 0.5 µm per 100 parts by weight of the total of the tetracalcium phosphate particles (A), the calcium hydrogen phosphate particles (B), and the calcium carbonate particles (C).

The dentinal tubule sealing material of the present invention preferably further includes 0.01 to 5 parts by weight of a fluorine compound (F), calculated as fluorine ion, per 100 parts by weight of the dentinal tubule sealing material.

The dentinal tubule sealing material of the present invention preferably further includes 0.5 to 15 parts by weight of an alkali metal phosphate (G) per 100 parts by weight of the total of the tetracalcium phosphate particles (A), the calcium hydrogen phosphate particles (B), and the calcium carbonate particles (C). The alkali metal phosphate (G) is preferably at least one selected from the group consisting of disodium hydrogen phosphate and sodium dihydrogen phosphate.

Advantageous Effects of Invention

According to the present invention, there is provided a dentinal tubule sealing material excellent in durability of dentinal tubule sealing performance and also in storage stability.

DESCRIPTION OF EMBODIMENTS

The present invention is a dentinal tubule sealing material including tetracalcium phosphate particles (A), calcium hydrogen phosphate particles (B), calcium carbonate particles (C), and a non-aqueous dispersant (D), the dentinal tubule sealing material being characterized by including 5 to 75 parts by weight of the tetracalcium phosphate particles (A), 10 to 70 parts by weight of the calcium hydrogen phosphate particles (B), and 2 to 50 parts by weight of the calcium carbonate particles (C) per 100 parts by weight of the total of the tetracalcium phosphate particles (A), the calcium hydrogen phosphate particles (B), and the calcium carbonate particles (C).

The tetracalcium phosphate particles (A) and the calcium hydrogen phosphate particles (B) are known to undergo curing and conversion to hydroxyapatite when they together are reacted with water. Additionally, the calcium hydrogen phosphate particles (B) and a phosphorus-free calcium compound (e.g., calcium carbonate, calcium oxide, calcium hydroxide, etc.) are also known to undergo curing and conversion to hydroxyapatite when they together are reacted with water.

In developing a dentinal tubule sealing material excellent in durability of dentinal tubule sealing performance and storage stability, the present inventors have found for a dentinal tubule sealing material including the tetracalcium phosphate particles (A), the calcium hydrogen phosphate particles (B), the calcium carbonate particles (C), and the non-aqueous dispersant (D) that the durability of dentinal tubule sealing performance and the storage stability of the material are uniquely improved only when the tetracalcium phosphate particles (A), the calcium hydrogen phosphate particles (B), and the calcium carbonate particles (C) are contained in specified amounts relative to the total of the tetracalcium phosphate particles (A), the calcium hydrogen phosphate particles (B), and the calcium carbonate particles (C). As demonstrated by Examples and Comparative Examples given later, a dentinal tubule sealing material including only a combination of the tetracalcium phosphate particles (A) and the calcium hydrogen phosphate particles (B) or a dentinal tubule sealing material including only a combination of the calcium hydrogen phosphate particles (B) and a phosphorus-free calcium compound is inferior in durability of dentinal tubule sealing performance and in storage stability. Also, the use of particles of various phosphorus-free calcium compounds instead of the calcium carbonate particles (C) leads to a low durability of the resulting dentinal tubule sealing product. Thus, it is primarily important, as in the present invention, to use a combination of specified components including the tetracalcium phosphate particles (A), the calcium hydrogen phosphate particles (B), and the calcium carbonate particles (C). Furthermore, it is important that the content of the tetracalcium phosphate particles (A) is 5 to 75 parts by weight, the content of the calcium hydrogen phosphate particles (B) is 10 to 70 parts by weight, and the content of the calcium carbonate particles (C) is 2 to 50 parts by weight, per 100 parts by weight of the total of the tetracalcium phosphate particles (A), the calcium hydrogen phosphate particles (B), and the calcium carbonate particles (C).

In the context of the present invention, "durability of dentinal tubule sealing performance" (or "durability of the resulting dentinal tubule sealing product") refers to the property of the resulting dentinal tubule sealing product to show resistance to acid over a long period of time.

The mechanism by which the dentinal tubule sealing material of the present invention seals dentinal tubules and inhibits hypersensitivity can be understood as follows. When the dentinal tubule sealing material is applied to an affected area where dentinal tubules are open, the tetracalcium phosphate particles (A), the calcium hydrogen phosphate particles (B), and the calcium carbonate particles (C) physically seal the openings of the dentinal tubules. After that, the tetracalcium phosphate particles (A), the calcium hydrogen phosphate particles (B), and the calcium carbonate particles (C) sealing the dentinal tubules react with water as a result of gargling during treatment or contact with saliva and undergo conversion to hydroxyapatite, which improves the durability of the resulting sealing product. The dentinal tubule sealing material of the present invention can thus be expected to offer good durability (acid resistance) of the resulting dentinal tubule sealing product and long-lasting effect on hypersensitivity inhibition in an oral cavity which is prone to acid generation.

The tetracalcium phosphate particles (A) used in the present invention are not particularly limited, and preferably have an average particle diameter of 0.5 to 10 µm. When the average particle diameter is less than 0.5 µm, the tetracalcium phosphate particles (A) are so excessively dissolved that the resulting aqueous solution has a high pH. This may hinder smooth precipitation of hydroxyapatite, thereby reducing the durability of the resulting sealing product. The average particle diameter is preferably 1.0 µm or more and more preferably 2.0 µm or more. When the average particle diameter is more than 10 µm, the particle diameter is too large relative to the diameter of dentinal tubules, which may reduce the initial performance of dentinal tubule sealing. The average particle diameter is preferably 8.0 µm or less and more preferably 6.0 µm or less. Herein, the average particle diameter of the tetracalcium phosphate particles (A) used in the present invention is a median diameter calculated based on measurement performed using a laser diffraction particle size distribution analyzer.

The method for producing the tetracalcium phosphate particles (A) is not particularly limited. Commercially-available tetracalcium phosphate particles may be used as such or may be used after adjustment of their particle diameters by appropriate pulverization. For pulverization, a pulverization apparatus such as a ball mill, a grinder, or a jet mill can be used. Alternatively, the tetracalcium phosphate particles (A) may be obtained by pulverizing commercially-available tetracalcium phosphate particles together with a liquid medium such as an alcohol using a grinder, a ball mill or the like so as to prepare a slurry, and then drying the obtained slurry. Preferred as the pulverization apparatus used in this case is a ball mill. As the material of the pot and balls, there is preferably employed alumina or zirconia. The particles prepared through pulverization as above usually have irregular shapes.

In the dentinal tubule sealing material of the present invention, the content of the tetracalcium phosphate particles (A) is 5 to 75 parts by weight per 100 parts by weight of the total of the tetracalcium phosphate particles (A), the calcium hydrogen phosphate particles (B), and the calcium carbonate particles (C). When the content is less than 5 parts by weight, the resulting sealing product has reduced durability. The content of the tetracalcium phosphate particles (A) is preferably 15 parts by weight or more and more preferably 25 parts by weight or more per 100 parts by weight of the above-mentioned total amount. Also when the content of the tetracalcium phosphate particles (A) is more than 75 parts by weight, the resulting sealing product has reduced durability. The content of the tetracalcium phosphate particles (A) is preferably 65 parts by weight or less and more preferably 55 parts by weight or less per 100 parts by weight of the above-mentioned total amount.

The calcium hydrogen phosphate particles (B) used in the present invention are not particularly limited. Particles of at least one selected from the group consisting of dibasic calcium phosphate anhydrous (which may be abbreviated as DCPA hereinafter), monobasic calcium phosphate anhydrous, dibasic calcium phosphate dihydrate, and monobasic calcium phosphate monohydrate are preferably used. Among these, particles of dibasic calcium phosphate anhydrous are more preferably used.

The average particle diameter of the calcium hydrogen phosphate particles (B) used in the present invention is preferably 0.1 to 7.5 µm. When the average particle diameter is less than 0.1 µm, the calcium hydrogen phosphate particles (B) are so excessively dissolved that the resulting aqueous solution has a low pH. This may hinder smooth precipitation of hydroxyapatite, thereby reducing the durability of the resulting sealing product. The average particle diameter is more preferably 0.5 µm or more. When the average particle diameter is more than 7.5 µm, the calcium hydrogen phosphate particles (B) are less soluble in water, which leads to excessive dissolution of the tetracalcium phosphate particles (A) and thereby a high pH of the resulting aqueous solution. This may hinder smooth precipitation of hydroxyapatite, thereby reducing the durability of the cured product. The average particle diameter is more preferably 5.0 µm or less and even more preferably 3.0 µm or less. The average particle diameter of the calcium hydrogen phosphate particles (B) is calculated in the same manner as the average particle diameter of the above-described tetracalcium phosphate particles (A).

The method for producing the calcium hydrogen phosphate particles (B) is not particularly limited. Commercially-available calcium hydrogen phosphate particles may be used as such or may, as in the case of the above-described tetracalcium phosphate particles (A), be used after adjustment of their particle diameters by appropriate pulverization.

In the dentinal tubule sealing material of the present invention, the content of the calcium hydrogen phosphate particles (B) is 10 to 70 parts by weight per 100 parts by weight of the total of the tetracalcium phosphate particles (A), the calcium hydrogen phosphate particles (B), and the calcium carbonate particles (C). The content less than 10 parts by weight leads to reduced initial performance of dentinal tubule sealing and also to reduced durability of the resulting sealing product. The content of the calcium hydrogen phosphate particles (B) is preferably 15 parts by weight or more and more preferably 30 parts by weight or more per 100 parts by weight of the above-mentioned total amount. When the content of the calcium hydrogen phosphate particles (B) is more than 70 parts by weight, the resulting sealing product has reduced durability. The content of the calcium hydrogen phosphate particles (B) is preferably 60 parts by weight or less and more preferably 50 parts by weight or less per 100 parts by weight of the above-mentioned total amount.

The calcium carbonate particles (C) constitute an important component for providing high storage stability of the dentinal tubule sealing material and high durability of the resulting sealing product. The non-use of the calcium carbonate particles (C) leads to low storage stability of the dentinal tubule sealing material and low durability of the resulting sealing product. Also, using a phosphorus-free calcium compound such as calcium oxide and calcium hydroxide instead of the calcium carbonate particles (C) leads to low durability of the resulting sealing product and to reduced initial performance of dentinal tubule sealing.

The average particle diameter of the calcium carbonate particles (C) is preferably 0.1 to 12 µm. When the average particle diameter is less than 0.1 µm, the calcium carbonate particles (C) are so excessively dissolved that the resulting aqueous solution has a high pH. This may hinder smooth precipitation of hydroxyapatite, thereby reducing the durability of the resulting sealing product. The average particle diameter is preferably 0.5 µm or more and more preferably 1.0 µm or more. When the average particle diameter is more than 12 µm, the particle diameter is too large relative to the diameter of dentinal tubules, which may reduce the performance of dentinal tubule sealing. The average particle diameter is preferably 8.0 µm or less and more preferably 5.0 µm or less. The average particle diameter of the calcium carbonate particles (C) is calculated in the same manner as the average particle diameter of the above-described tetracalcium phosphate particles (A).

The method for producing the calcium carbonate particles (C) is not particularly limited. Commercially-available calcium carbonate particles may be used as such or may, as in the case of the above-described tetracalcium phosphate particles (A), be used after adjustment of their particle diameters by appropriate pulverization.

In the dentinal tubule sealing material of the present invention, the content of the calcium carbonate particles (C) is 2 to 50 parts by weight per 100 parts by weight of the total of the tetracalcium phosphate particles (A), the calcium hydrogen phosphate particles (B), and the calcium carbonate particles (C). When the content is less than 2 parts by weight, the resulting sealing product has reduced durability. The content of the calcium carbonate particles (C) is preferably 3.5 parts by weight or more and more preferably 5 parts by weight or more per 100 parts by weight of the above-mentioned total amount. The content of the calcium carbonate particles (C) more than 50 parts by weight leads to reduced initial performance of dentinal tubule sealing and to reduced durability of the resulting sealing product. The content of the calcium carbonate particles (C) is preferably 40 parts by weight or less and more preferably 35 parts by weight or less per 100 parts by weight of the above-mentioned total amount.

The non-aqueous dispersant (D) is a component for preparing the dentinal tubule sealing material in the form of a paste and providing high ease of use. The non-aqueous dispersant (D) used in the present invention is not particularly limited, and is preferably at least one selected from the group consisting of: polyhydric alcohols such as glycerin, ethylene glycol, propylene glycol, and diglycerin; and polyethers such as polyethylene glycol (which may hereinafter be abbreviated as "PEG") and polypropylene glycol. Among these, glycerin, ethylene glycol, propylene glycol, and polyethylene glycol are particularly preferably used. The content of the non-aqueous dispersant (D) is preferably 20 to 90 parts by weight per 100 parts by weight of the dentinal tubule sealing material of the present invention. When the content is less than 20 parts by weight, the paste may have a high viscosity and hence reduced handling properties. The content of the non-aqueous dispersant (D) is more preferably 25 parts by weight or more and even more preferably 30 parts by weight or more per 100 parts by weight of the dentinal tubule sealing material. When the content of the non-aqueous dispersant (D) is more than 90 parts by weight, the dentinal tubule sealing performance may be reduced. The content of the non-aqueous dispersant (D) is more preferably 85 parts by weight or less and even more preferably 82 parts by weight or less per 100 parts by weight of the dentinal tubule sealing material.

It is preferable for the dentinal tubule sealing material of the present invention to further include silica and/or metal oxide particles (E) having an average particle diameter of 0.002 to 0.5 µm. Adding the silica and/or metal oxide particles (E) having an average particle diameter of 0.002 to 0.5 µm further improves the dentinal tubule sealing performance. The silica and/or metal oxide particles (E) are not particularly limited. Specific examples of the metal oxide particles include particles of titania, alumina, zirconia, cerium oxide, hafnium oxide, yttrium oxide, beryllium oxide, niobium oxide, lanthanum oxide, bismuth oxide, tin oxide, zinc oxide, iron oxide, molybdenum oxide, nickel oxide, ytterbium oxide, samarium oxide, europium oxide, praseodymium oxide, magnesium oxide, and neodymium oxide. In the present invention, particles of a composite oxide containing silicon element and a metal element or containing two different metal elements can also be preferably used as the silica and/or metal oxide particles (E) having an average particle diameter of 0.002 to 0.5 µm. Silica is a preferred material of the silica and/or metal oxide particles (E) having an average particle diameter of 0.002 to 0.5 µm, and metal oxides preferred as the material of the particles (E) are titania, alumina, and zirconia.

The average particle diameter of the silica and/or metal oxide particles (E) used in the present invention is 0.002 to 0.5 μm. When the average particle diameter of the silica and/or metal oxide particles (E) is less than 0.002 μm, the dentinal tubule sealing material has a higher viscosity and hence reduced ease of use. The average particle diameter is preferably 0.003 μm or more, and more preferably 0.005 μm or more. When the average particle diameter of the silica and/or metal oxide particles (E) is more than 0.5 μm, the dentinal tubule sealing ratio is reduced. The average particle diameter is preferably 0.2 μm or less and more preferably 0.1 μm or less. The average particle diameter of the silica and/or metal oxide particles (E) is calculated as follows: a photograph of primary particles dispersed in an epoxy resin is taken by a transmission electron microscope, the diameters of 100 or more primary particles randomly selected from the photograph are measured, and their arithmetic mean is calculated as the average particle diameter.

In the dentinal tubule sealing material of the present invention, the content of the silica and/or metal oxide particles (E) having an average particle diameter of 0.002 to 0.5 μm is 0.1 to 100 parts by weight per 100 parts by weight of the total of the tetracalcium phosphate particles (A), the calcium hydrogen phosphate particles (B), and the calcium carbonate particles (C). When the content is less than 0.1 parts by weight, the improving effect on the dentinal tubule sealing performance is reduced. The content of the silica and/or metal oxide particles (E) is preferably 1 part by weight or more and more preferably 2 parts by weight or more per 100 parts by weight of the above-mentioned total amount. When the content of the silica and/or metal oxide particles (E) is more than 100 parts by weight, the dentinal tubule sealing material has an increased viscosity and hence lower ease of use.

The content of the silica and/or metal oxide particles (E) is preferably 75 parts by weight or less and more preferably 50 parts by weight or less per 100 parts by weight of the above-mentioned total amount.

It is preferable for the dentinal tubule sealing material of the present invention to further include a fluorine compound (F), in view of acid resistance. The fluorine compound (F) is not particularly limited, and examples thereof include sodium fluoride, potassium fluoride, ammonium fluoride, lithium fluoride, cesium fluoride, magnesium fluoride, calcium fluoride, strontium fluoride, barium fluoride, copper fluoride, zirconium fluoride, aluminum fluoride, tin fluoride, sodium monofluorophosphate, potassium monofluorophosphate, hydrofluoric acid, titanium sodium fluoride, titanium potassium fluoride, hexylamine hydrofluoride, laurylamine hydrofluoride, glycine hydrofluoride, alanine hydrofluoride, fluorosilanes, and diamine silver fluoride. Among these, sodium fluoride, sodium monofluorophosphate, and tin fluoride are preferably used in view of safety.

In the dentinal tubule sealing material of the present invention, the content of the fluorine compound (F), calculated as fluorine ion content, is 0.01 to 5 parts by weight per 100 parts by weight of the dentinal tubule sealing material. When the content is less than 0.01 parts by weight, there is no improvement in the acid resistance of the dentinal tubule sealing material. The content of the fluorine compound (F), calculated as fluorine ion content, is preferably 0.02 parts by weight or more per 100 parts by weight of the dentinal tubule sealing material. When the content of the fluorine compound (F), calculated as fluorine ion content, is more than 5 parts by weight, the safety of the sealing material may be deteriorated. The content of the fluorine compound (F), calculated as fluorine ion content, is preferably 3 parts by weight or less per 100 parts by weight of the dentinal tubule sealing material.

It is preferable for the dentinal tubule sealing material of the present invention to further include an alkali metal phosphate (G) so that the resulting sealing product has further improved durability. The alkali metal phosphate (G) used in the present invention is not particularly limited, and examples thereof include disodium hydrogen phosphate, dipotassium hydrogen phosphate, lithium dihydrogen phosphate, sodium dihydrogen phosphate, potassium dihydrogen phosphate, trisodium phosphate, tripotassium phosphate, and hydrates thereof. One or more of these examples are used. In particular, it is preferable for the alkali metal phosphate (G) to be at least one selected from the group consisting of disodium hydrogen phosphate and sodium dihydrogen phosphate in view of safety and of high availability of a high-purity source material.

In the dental dentinal tubule sealing material of the present invention, the content of the alkali metal phosphate (G) is 0.5 to 15 parts by weight per 100 parts by weight of the total of the tetracalcium phosphate particles (A), the calcium hydrogen phosphate particles (B), and the calcium carbonate particles (C). When the content is less than 0.5 parts by weight, the addition of the alkali metal phosphate (G) offers little improvement in the durability of the resulting sealing product. The content of the alkali metal phosphate (G) is preferably 1 part by weight or more and more preferably 2 parts by weight or more per 100 parts by weight of the above-mentioned total amount. When the content of the alkali metal phosphate (G) is more than 15 parts by weight, the initial performance of dentinal tubule sealing is reduced. The content of the alkali metal phosphate (G) is preferably 12 parts by weight or less and more preferably 10 parts by weight or less per 100 parts by weight of the above-mentioned total amount.

The alkali metal phosphate (G) is preferably in the form of particles having an average particle diameter of 1.0 to 12 μm. When the average particle diameter of the alkali metal phosphate (G) is less than 1.0 μm, its dissolution by contact with water is so excessively rapid that the concentration of phosphate ions is high. This may cause loss of balance between supply of calcium ions and supply of phosphate ions, resulting in a reduced rate of precipitation of hydroxyapatite. The average particle diameter of the alkali metal phosphate (G) is more preferably 3.0 μm or more. When the average particle diameter of the alkali metal phosphate (G) is more than 12 μm, the alkali metal phosphate (G) is less soluble by contact with water, so the rate of precipitation of hydroxyapatite may become lower. The average particle diameter of the alkali metal phosphate (G) is more preferably 8.0 μm or less. The average particle diameter of the alkali metal phosphate (G) is calculated in the same manner as the average particle diameter of the above-described tetracalcium phosphate particles (A).

The method for producing the alkali metal phosphate (G) is not particularly limited. A commercially-available alkali metal phosphate may be used as such or may, as in the case of the above-described tetracalcium phosphate particles (A), be used after adjustment of the particle diameter by appropriate pulverization.

To the extent that the effect of the present invention is not impaired, the dentinal tubule sealing material of the present invention may optionally contain a component other than the tetracalcium phosphate particles (A), the calcium hydrogen phosphate particles (B), the calcium carbonate particles (C), the non-aqueous dispersant (D), the silica and/or metal oxide particles (E) having an average particle diameter of 0.002 to 0.5 μm, the fluorine compound (F), and the alkali metal phosphate (G). For example, water, a thickener, or an X-ray contrast agent may be contained.

The thickener is not particularly limited, and an exemplary thickener includes one or more selected from the following polymers: polysaccharides such as carboxymethyl cellulose, sodium carboxymethyl cellulose, hydroxypropyl cellulose, hydroxypropyl methylcellulose, polyvinyl alcohol, polyacrylic acid, polystyrene sulfonic acid, polystyrene sulfonate, polyglutamic acid, polyglutamate, polyaspartic acid, polyaspartate, poly-L-lysine, poly-L-lysine salt, starches other than cellulose, alginic acid, alginate, carrageenan, guar gum, xanthan gum, cellulose gum, hyaluronic acid, hyaluronate, pectin, pectate, chitin, and chitosan; acidic polysaccharide esters such as propylene glycol alginate; and proteins such as collagen, gelatin, and derivatives thereof.

The X-ray contrast agent is not particularly limited, and an exemplary X-ray contrast agent includes one or more selected from barium sulfate, bismuth subcarbonate, bismuth oxide, zirconium oxide, ytterbium fluoride, iodoform, barium apatite, barium titanate, lanthanum glass, barium glass, strontium glass, etc.

Where necessary, there may also be added: a sugar alcohol such as xylitol, sorbitol, and erythritol; or an artificial sweetener such as aspartame, acesulfame potassium, sweet root extract, saccharin, and saccharin sodium. Furthermore, any pharmacologically acceptable agent may be contained. There may be contained: an antibacterial agent typified by cetylpyridinium chloride; an antiseptic agent; an anticancer agent; an antibiotic substance; a blood circulation improving drug such as actosin and PEG1; a growth factor such as bFGF, PDGF, and BMP; cells which promote hard tissue formation, such as osteoblast cells, odontoblast cells, undifferentiated marrow-derived stem cells, embryonic stem (ES) cells, induced pluripotent stem (iPS) cells prepared by dedifferentiation of differentiated cells such as differentiated fibroblast cells through gene transfer, and cells prepared by differentiating those cells.

The dentinal tubule sealing material of the present invention is obtained as a paste including at least the tetracalcium phosphate particles (A), the calcium hydrogen phosphate particles (B), the calcium carbonate particles (C), and the non-aqueous dispersant (D). The paste can be prepared as a one-part product and is excellent in storage stability. Additionally, the paste has good handling properties.

The method for preparing the paste including at least the tetracalcium phosphate particles (A), the calcium hydrogen phosphate particles (B), the calcium carbonate particles (C), and the non-aqueous dispersant (D), is not particularly limited. For example, the paste can be obtained by mixing with a biaxial kneader, a triaxial kneader, a planetary kneader, or the like.

The dentinal tubule sealing material of the present invention is used by being applied to a dentin surface or more preferably by being rubbed on a dentin surface. The rubbing can be done only by scrubbing the material on the dentin surface with a microbrush, a cotton applicator, a rubber cup, or a toothbrush for about 30 seconds. This result in the formation of a sealing product reaching a depth of about 5 μm in dentinal tubules. The sealing product shows high acid resistance. Thus, the dentinal tubule sealing material of the present invention yields high durability of dentinal tubule sealing performance.

Examples of preferred embodiments of the dentinal tubule sealing material of the present invention include a tooth surface treating material, a dentifrice, and a dentin hypersensitivity inhibitor. The use of the dentinal tubule sealing material of the present invention in the above applications is expected to provide a long-lasting effect on hypersensitivity inhibition since the sealing product in dentinal tubules has good durability. Additionally, the good handling properties and storage stability offer high ease of use during treatment. Furthermore, the dentinal tubule sealing material of the present invention is excellent in biocompatibility since it converts to hydroxyapatite through contact with water in an oral cavity and unites with a tooth in an area to which it is applied.

The present invention encompasses embodiments obtainable by combining the above-described features in various manners within the technical scope of the present invention as long as such embodiments exert the effect of the present invention.

EXAMPLES

Hereinafter, the present invention will be described in detail by way of Examples and Comparative Examples. It should be noted that the present invention is not limited to these examples.

[Method for Measuring Average Particle Diameter]

In the present examples, the average particle diameters of the particles other than the silica and/or metal oxide particles (E) were each determined as a median diameter calculated from the result of particle size distribution measurement using a laser diffraction particle size distribution analyzer ("SALD-2100" manufactured by Shimadzu Corporation). The average particle diameter of the silica and/or metal oxide particles (E) was calculated by the method specified in the above description.

[Preparation of Each Component]

(1) Preparation of Tetracalcium Phosphate Particles (A)

Tetracalcium phosphate particles manufactured by TAIHEI CHEMICAL INDUSTRIAL CO., LTD. as such were used as the tetracalcium phosphate particles (A) (average particle diameter: 5.2 μm, 8.8 μm) in the present examples.

Tetracalcium phosphate particles (average particle diameter: 1.1 μm) were prepared in the manner described hereinafter. In a 400 ml milling pot made of alumina ("Type A-3 HD pot mill" manufactured by Nikkato Corp.) were put 50 g of commercially-available tetracalcium phosphate particles (manufactured by TAIHEI CHEMICAL INDUSTRIAL CO., LTD. and having an average particle diameter of 5.2 μm), 120 g of 95% ethanol ("Ethanol (95)" manufactured by Wako Pure Chemical Industries, Ltd.), and 240 g of zirconia balls having a diameter of 10 mm. Wet milling was performed at a rotation speed of 120 rpm for 24 hours to obtain a slurry, from which the ethanol was distilled off using a rotary evaporator and which was then dried at 60° C. for 6 hours and further vacuum-dried at 60° C. for 24 hours. Thus, the tetracalcium phosphate particles were obtained.

(2) Preparation of Calcium Hydrogen Phosphate Particles (B)

Particles of dibasic calcium phosphate anhydrous (average particle diameter: 1.1 μm) manufactured by TAIHEI CHEMICAL INDUSTRIAL CO., LTD. as such were used as one example of the calcium hydrogen phosphate particles (B) in the present examples.

Particles of dibasic calcium phosphate anhydrous (average particle diameter: 5.0 μm) were obtained as follows: 50 g of commercially-available particles of dibasic calcium phosphate anhydrous (manufactured by Wako Pure Chemical Industries, Ltd. and having an average particle diameter of 10.2 μm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 7 hours to obtain a slurry, from which the ethanol was distilled off using a rotary evaporator and which was then dried at 60° C. for 6 hours and further vacuum-dried at 60° C. for 24 hours.

Particles of dibasic calcium phosphate anhydrous (average particle diameter: 0.3 μm) were obtained as follows: 50 g of commercially-available particles of dibasic calcium phosphate anhydrous (manufactured by Wako Pure Chemical Industries, Ltd. and having an average particle diameter of 10.2 μm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 40 hours to obtain a slurry, from which the ethanol was distilled off using a rotary evaporator and which was then dried at 60° C. for 6 hours and further vacuum-dried at 60° C. for 24 hours.

(3) Preparation of Calcium Carbonate Particles (C)

Calcium carbonate particles manufactured by YABASHI INDUSTRIES CO., LTD. as such were used as calcium carbonate particles (average particle diameter: 2.6 μm) in the present examples.

Calcium carbonate particles (average particle diameter: 0.5 μm) were obtained as follows: 50 g of commercially-available calcium carbonate particles (manufactured by Konoshima Chemical Co., Ltd. and having an average particle diameter of 25.4 μm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 35 hours to obtain a slurry, from which the ethanol was distilled off using a rotary evaporator and which was then dried at 60° C. for 6 hours and further vacuum-dried at 60° C. for 24 hours.

Calcium carbonate particles (average particle diameter: 10.2 μm) were obtained as follows: 50 g of commercially-available calcium carbonate particles (manufactured by Konoshima Chemical Co., Ltd. and having an average particle diameter of 25.4 μm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 5 hours to obtain a slurry, from which the ethanol was distilled off using a rotary evaporator and which was then dried at 60° C. for 6 hours and further vacuum-dried at 60° C. for 24 hours.

(4) Preparation of Non-Aqueous Dispersant (D)

Glycerin, polyethylene glycol (molecular weight=400), and polyethylene glycol (molecular weight=4000) manufactured by Wako Pure Chemical Industries, Ltd. as such were used as examples of the non-aqueous material (D).

(5) Preparation of Silica and/or Metal Oxide Particles (E) Having Average Particle Diameter of 0.002 to 0.5 μm Silica particles manufactured by Nippon Aerosil Co., Ltd. (Aerosil 300, having an average particle diameter of 0.007 μm) as such were used as an example of the silica and/or metal oxide particles (E) having an average particle diameter of 0.002 to 0.5 μm in the present examples.

(6) Preparation of Fluorine Compound (F)

Sodium fluoride manufactured by Wako Pure Chemical Industries, Ltd. as such was used as an example of the fluorine compound (F) in the present examples.

(7) Preparation of Alkali Metal Phosphate (G)

Disodium hydrogen phosphate particles (average particle diameter: 5.2 μm) used as one example of the alkali metal phosphate (G) in the present examples were obtained by processing commercially-available disodium hydrogen phosphate (manufactured by Wako Pure Chemical Industries, Ltd.) once by Nano Jetmizer (NJ-100, manufactured by Aisin Nanotechnology) under the following conditions: source material supply pressure =0.7 MPa, crushing pressure=0.7 MPa, through put=8 kg/hr).

Calcium hydroxide, calcium oxide, calcium silicate, calcium nitrate, and calcium oxalate manufactured by Wako Pure Chemical Industries, Ltd. as such were used as those in Comparative Examples.

[Preparation of Dentinal Tubule Sealing Material]

The tetracalcium phosphate particles (A), the calcium hydrogen phosphate particles (B), the calcium carbonate particles (C), the non-aqueous dispersant (D), optionally the silica and/or metal oxide particles (E) having an average particle diameter of 0.002 to 0.5 μm, optionally the fluorine compound (F), and optionally particles of the alkali metal phosphate (G), which were weighed to give compositions shown in Tables 1 to 3, were put in a universal mixing stirrer ("STM-08" manufactured by Dalton Co., Ltd.) and mixed at a rotation speed of 130 rpm and a revolution speed of 37 rpm for 60 minutes to obtain dentinal tubule sealing materials.

[Test of Dentinal Tubule Sealing Ratio]

(1) Preparation of Disc of Bovine Tooth

The buccal center of a healthy bovine incisor was ground with waterproof abrasive paper No. 80 and then No. 1000 to have the dentin exposed and form the bovine tooth into a disc having a diameter of about 7 mm and a thickness of 2 mm.

The ground surface of the bovine tooth was further ground with wrapping films No. 1200, No. 3000, and then No. 8000 (manufactured by Sumitomo 3M). Next, the bovine tooth was immersed in a solution prepared by five-fold dilution of a 0.5 M EDTA solution (manufactured by Wako Pure Chemical Industries, Ltd.) for 30 minutes, then washed with water for 60 seconds, subjected to a 10% sodium hypochlorite solution (Neo Cleaner "SEKINE" manufactured by NEO DENTAL CHEMICAL PRODUCTS CO., LTD.) for 60 seconds, and finally washed with water for 60 seconds.

(2) Preparation of Artificial Saliva

Sodium chloride (8.77 g, 150 mmol), potassium dihydrogen phosphate (122 mg, 0.9 mmol), calcium chloride (166 mg, 1.5 mmol), and Hepes (4.77 g, 20 mmol) were each weighed into a weighing dish, and sequentially added to about 800 ml of distilled water held in a 2000 ml beaker under stirring. After confirmation of complete dissolution of the solutes, a 10% aqueous sodium hydroxide solution was added dropwise with simultaneous measurement of the acidity of the solution by a pH meter (F55, manufactured by HORIBA, Ltd.) to adjust the pH to 7.0.

(3) Sealing of Dentinal Tubules and Acid Immersion

A paste of each dentinal tubule sealing material weighed to 0.1 g was put onto the buccal dentin surface of the disc of bovine tooth obtained in (1), and rubbed over a 5-mm-diameter area of the central portion of the treated dentin surface using Microbrush Regular (manufactured by Microbrush Co.) for 30 seconds. Thereafter, the paste of the dentinal tubule sealing material on the surface of the disc of bovine tooth was removed with distilled water, and the disc of bovine tooth was immersed in the artificial saliva obtained in (2) at 37° C. for 24 hours to obtain a test piece (A) for SEM observation. For evaluation of the post-acid immersion dentinal tubule sealing ratio, the disc of bovine tooth treated with the above dentinal tubule sealing material and immersed in the artificial saliva at 37° C. for 24 hours was horizontally immersed in 30 mL of a 0.1 M lactic acid buffer solution (pH=4.75) held in a separate container at 37° C. for 10 minutes, with the surface treated with the dentinal tubule sealing material facing upward. Thereafter, the disc of bovine tooth was washed with distilled water, and then immersed in the artificial saliva at 37° C. The acid immersion was performed in a once per day cycle. This operation was repeated for 14 days to obtain a test piece (B) for SEM observation.

(4) SEM Observation

The test pieces (A) and (B) obtained in (3) were dried at room temperature under reduced pressure for 1 hour and subjected to metal vapor deposition, after which the surfaces treated with the dentinal tubule sealing material were each observed at three arbitrarily-selected points using a scanning electron microscope (S-3500N, manufactured by Hitachi High-Technologies Corporation) at a magnification of 3000 times. The dentinal tubule sealing ratio in each observation field of view was calculated according to the formula given below, and the values obtained for the three points were averaged. The number of tests performed was 5 (n=5), and the values obtained through all the tests were averaged, and the average was determined as the dentinal tubule sealing ratio. The dentinal tubule sealing ratio for the test piece (A) was shown as "Dentinal tubule sealing ratio (initial)" in the tables below. The dentinal tubule sealing ratio for the test piece (B) was shown as "Dentinal tubule sealing ratio (post-acid immersion)" in the tables below.

Dentinal tubule sealing ratio (%)={(Number of sealed dentinal tubules)/(Number of total dentinal tubules)}×100

In the tables below, the values of the decrease ratio (%) of the dentinal tubule sealing ratio are those calculated by the following formula.

Decrease ratio (%) of dentinal tubule sealing ratio=100−{[Dentinal tubule sealing ratio (post-acid immersion)/Dentinal tubule sealing ratio (initial)]×100}

[Test of Handling Properties]

(1) Handling Properties

The pastes composed as shown in Tables 1 to 3 were each accurately weighed to 0.1 g, and applied to artificial teeth of a dental cast using Microbrush Regular (Microbrush Co.). The performance in terms of the application was evaluated according to the following criteria.

(2) Evaluation Criteria of Handling Properties

A: Application can easily be achieved with Microbrush Regular within 30 seconds per tooth. Additionally, the paste is securely held on tooth surfaces without running down during application.

B: Application can be achieved with Microbrush Regular within 30 seconds per tooth. However, the paste has poor stretchability and is somewhat difficult to apply, or the paste is somewhat soft and somewhat likely to run down during application.

C: The paste is hard so that it takes more than 30 seconds but 60 seconds or less per tooth to apply the paste with Microbrush Regular. Or the paste is soft and likely to run down during application.

D: The paste is so excessively hard that application with Microbrush Regular requires more than 60 seconds per tooth. Or the paste is so excessively soft that the paste rapidly runs down and cannot be applied.

A to C correspond to the levels acceptable for practical use.

[Storage Stability Test]

(1) Storage Stability

The obtained pastes composed as shown in Tables 1 to 3 were each accurately weighed to 5 g into a glass sample tube and allowed to stand at 25° C.

The storage stability of each paste was evaluated according to the following criteria.

A: The paste maintains good quality for more than 3 months after the preparation.

B: The paste maintains good quality for 1 to 3 months after the preparation.

C: The paste maintains good quality for 2 weeks or more but less than 1 month after the preparation.

D: Curing or viscosity increase occurs in 1 day after the preparation, and the pasty state cannot be maintained.

Examples 1 to 30

Dentinal tubule sealing materials composed as shown in Tables 1 to 3 were prepared by the procedures described above, and were evaluated for the initial dentinal tubule sealing performance, the post-acid immersion dentinal tubule sealing performance, the handling properties, and the storage stability. The evaluation results obtained are collectively shown in Tables 1 to 3.

Comparative Examples 1 to 13

Compositions as shown in Tables 4 to 5 were prepared by the same procedures as those in Examples above, and were evaluated for the initial dentinal tubule sealing performance, the post-acid immersion dentinal tubule sealing performance, the handling properties, and the storage stability. The evaluation results obtained are collectively shown in Tables 4 and 5.

TABLE 1

| | | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|---|
| A | TTCP (D50: 1.1 μm) | (parts by weight) | | | | | | | | | | | |
| | TTCP (D50: 5.2 μm) | (parts by weight) | 20.5 | 20.5 | 30.8 | 10.3 | 6.2 | 2.5 | 9.0 | 7.5 | 3.8 | 7.5 | 4.5 |
| | TTCP (D50: 8.8 μm) | (parts by weight) | | | | | | | | | | | |
| B | DCPA (D50: 0.3 μm) | (parts by weight) | | | | | | | | | | | |
| | DCPA (D50: 1.1 μm) | (parts by weight) | 20.5 | 20.5 | 30.8 | 10.3 | 6.2 | 7.5 | 5.3 | 2.5 | 9.0 | 7.0 | 4.5 |
| | DCPA (D50: 5.0 μm) | (parts by weight) | | | | | | | | | | | |

TABLE 1-continued

|   |   |   | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|---|
| C | Calcium carbonate (D50: 0.5 μm) | (parts by weight) | | | | | | | | | | | |
|   | Calcium carbonate (D50: 2.6 μm) | (parts by weight) | 9.0 | 9.0 | 13.4 | 4.4 | 2.6 | 5.0 | 0.7 | 5.0 | 2.2 | 0.5 | 6.0 |
|   | Calcium carbonate (D50: 10.2 μm) | (parts by weight) | | | | | | | | | | | |
| D | Glycerin | (parts by weight) | 40.0 | 50.0 | 20.0 | 60.0 | 60.0 | 60.0 | 60.0 | 60.0 | 60.0 | 60.0 | 60.0 |
|   | PEG 400 | (parts by weight) | | | | | | | | | | | |
|   | PEG 4000 | (parts by weight) | 10.0 | | 5.0 | 15.0 | 25.0 | 25.0 | 25.0 | 25.0 | 25.0 | 25.0 | 25.0 |
| E | Silica (Aerosil 300) | (parts by weight) | | | | | | | | | | | |
| F | Sodium fluoride | (parts by weight) | | | | | | | | | | | |
| G | Na$_2$HPO$_4$ (D50: 5.2 μm) | (parts by weight) | | | | | | | | | | | |
| Total | | (parts by weight) | 100.0 | 100.0 | 100.0 | 100.0 | 100.0 | 100.0 | 100.0 | 100.0 | 100.0 | 100.0 | 100.0 |
| Dentinal tubule sealing ratio (initial) | | (%) | 87.4 | 85.2 | 94.2 | 85.1 | 80.2 | 79.4 | 78.2 | 78.8 | 80.0 | 77.5 | 79.1 |
| Dentinal tubule sealing ratio (post-acid immersion) | | (%) | 70.6 | 71.3 | 75.1 | 69.8 | 65.8 | 59.8 | 59.3 | 57.7 | 60.1 | 57.8 | 58.4 |
| Decrease ratio of dentinal tubule sealing ratio | | (%) | 19.2 | 16.3 | 20.3 | 18.0 | 18.0 | 24.7 | 24.2 | 26.8 | 24.9 | 25.4 | 26.2 |
| Handling properties | | | A | A | B | A | A | A | A | A | A | A | A |
| Storage stability | | | A | B | A | A | A | A | A | A | A | A | A |
| Content of A per 100 parts by weight of total of A + B + C | | (parts by weight) | 41.0 | 41.0 | 41.1 | 41.2 | 41.3 | 16.7 | 60.0 | 50.0 | 25.3 | 50.0 | 30.0 |
| Content of B per 100 parts by weight of total of A + B + C | | (parts by weight) | 41.0 | 41.0 | 41.1 | 41.2 | 41.3 | 50.0 | 35.3 | 16.7 | 60.0 | 46.7 | 30.0 |
| Content of C per 100 parts by weight of total of A + B + C | | (parts by weight) | 18.0 | 18.0 | 17.8 | 17.6 | 17.4 | 33.3 | 4.7 | 33.3 | 14.7 | 3.3 | 40.0 |
| Content of E per 100 parts by weight of total of A + B + C | | (parts by weight) | 0 | 0 | 0 | 0 | 0 | 0 | 0 | 0 | 0 | 0 | 0 |
| Content of F calculated as fluorine ion content per 100 parts by weight of composition | | (parts by weight) | 0 | 0 | 0 | 0 | 0 | 0 | 0 | 0 | 0 | 0 | 0 |
| Content of G per 100 parts by weight of total of A + B + C | | (parts by weight) | 0 | 0 | 0 | 0 | 0 | 0 | 0 | 0 | 0 | 0 | 0 |

TABLE 2

|   |   |   | Example 12 | Example 13 | Example 14 | Example 15 | Example 16 | Example 17 | Example 18 | Example 19 | Example 20 | Example 21 |
|---|---|---|---|---|---|---|---|---|---|---|---|---|
| A | TTCP (D50: 1.1 μm) | (parts by weight) | | | | | | | 6.2 | | | |
|   | TTCP (D50: 5.2 μm) | (parts by weight) | 1.5 | 9.0 | 8.25 | 3.75 | 7.5 | 4.5 | | | 6.2 | 6.2 |
|   | TTCP (D50: 8.8 μm) | (parts by weight) | | | | | | | | 6.2 | | |
| B | DCPA (D50: 0.3 μm) | (parts by weight) | | | | | | | | | 6.2 | |
|   | DCPA (D50: 1.1 μm) | (parts by weight) | 7.5 | 5.3 | 1.5 | 10.5 | 7.2 | 4.5 | 6.2 | 6.2 | | |
|   | DCPA (D50: 5.0 μm) | (parts by weight) | | | | | | | | | | 6.2 |
| C | Calcium carbonate (D50: 0.5 μm) | (parts by weight) | | | | | | | | | | |
|   | Calcium carbonate (D50: 2.6 μm) | (parts by weight) | 6.0 | 0.7 | 5.25 | 0.75 | 0.3 | 6.0 | 2.6 | 2.6 | 2.6 | 2.6 |
|   | Calcium carbonate (D50: 10.2 μm) | (parts by weight) | | | | | | | | | | |
| D | Glycerin | (parts by weight) | 60.0 | 60.0 | 60.0 | 60.0 | 60.0 | 60.0 | 60.0 | 60.0 | 60.0 | 60.0 |
|   | PEG 400 | (parts by weight) | | | | | | | | | | |
|   | PEG 4000 | (parts by weight) | 25.0 | 25.0 | 25.0 | 25.0 | 25.0 | 25.0 | 25.0 | 25.0 | 25.0 | 25.0 |
| E | Silica (Aerosil 300) | (parts by weight) | | | | | | | | | | |
| F | Sodium fluoride | (parts by weight) | | | | | | | | | | |
| G | Na$_2$HPO$_4$ (D50: 5.2 μm) | (parts by weight) | | | | | | | | | | |
| Total | | (parts by weight) | 100.0 | 100.0 | 100.0 | 100.0 | 100.0 | 100.0 | 100.0 | 100.0 | 100.0 | 100.0 |
| Dentinal tubule sealing ratio (initial) | | (%) | 77.9 | 76.7 | 74.2 | 79.4 | 80.1 | 73.4 | 80.2 | 71.4 | 82.6 | 81.1 |
| Dentinal tubule sealing ratio (post-acid immersion) | | (%) | 54.6 | 53.6 | 52.9 | 55.4 | 55.2 | 49.6 | 60.2 | 54.7 | 61.1 | 60.9 |
| Decrease ratio of dentinal tubule sealing ratio | | (%) | 29.9 | 30.1 | 28.7 | 30.2 | 31.1 | 32.4 | 24.9 | 23.4 | 26.0 | 24.9 |

TABLE 2-continued

|  |  | Example 12 | Example 13 | Example 14 | Example 15 | Example 16 | Example 17 | Example 18 | Example 19 | Example 20 | Example 21 |
|---|---|---|---|---|---|---|---|---|---|---|---|
| Handling properties | | A | A | A | A | A | A | A | A | A | A |
| Storage stability | | A | A | A | A | A | A | A | A | A | A |
| Content of A per 100 parts by weight of total of A + B + C | (parts by weight) | 10.0 | 60.0 | 55.0 | 25.0 | 50.0 | 30.0 | 41.3 | 41.3 | 41.3 | 41.3 |
| Content of B per 100 parts by weight of total of A + B + C | (parts by weight) | 50.0 | 35.3 | 10.0 | 70.0 | 48.0 | 30.0 | 41.3 | 41.3 | 41.3 | 41.3 |
| Content of C per 100 parts by weight of total of A + B + C | (parts by weight) | 40.0 | 4.7 | 35.0 | 5.0 | 2.0 | 40.0 | 17.4 | 17.4 | 17.4 | 17.4 |
| Content of E per 100 parts by weight of total of A + B + C | (parts by weight) | 0 | 0 | 0 | 0 | 0 | 0 | 0 | 0 | 0 | 0 |
| Content of F calculated as fluorine ion content per 100 parts by weight of composition | (parts by weight) | 0 | 0 | 0 | 0 | 0 | 0 | 0 | 0 | 0 | 0 |
| Content of G per 100 parts by weight of total of A + B + C | (parts by weight) | 0 | 0 | 0 | 0 | 0 | 0 | 0 | 0 | 0 | 0 |

TABLE 3

|  |  |  | Example 22 | Example 23 | Example 24 | Example 25 | Example 26 | Example 27 | Example 28 | Example 29 | Example 30 |
|---|---|---|---|---|---|---|---|---|---|---|---|
| A | TTCP (D50: 1.1 μm) | (parts by weight) | | | | | | | | | |
|  | TTCP (D50: 5.2 μm) | (parts by weight) | 6.2 | 6.2 | 6.2 | 6.2 | 6.2 | 6.2 | 7.5 | 7.5 | 6.2 |
|  | TTCP (D50: 8.8 μm) | (parts by weight) | | | | | | | | | |
| B | DCPA (D50: 0.3 μm) | (parts by weight) | | | | | | | | | |
|  | DCPA (D50: 1.1 μm) | (parts by weight) | 6.2 | 6.2 | 6.2 | 6.2 | 6.2 | 6.2 | 2.5 | 7.2 | 6.2 |
|  | DCPA (D50: 5.0 μm) | (parts by weight) | | | | | | | | | |
| C | Calcium carbonate (D50: 0.5 μm) | (parts by weight) | 2.6 | | | | | | | | |
|  | Calcium carbonate (D50: 2.6 μm) | (parts by weight) | | | 2.6 | 2.6 | 2.6 | 2.6 | 5.0 | 0.3 | 2.6 |
|  | Calcium carbonate (D50: 10.2 μm) | (parts by weight) | | 2.6 | | | | | | | |
| D | Glycerin | (parts by weight) | 60.0 | 60.0 | 41.0 | 45.8 | 43.0 | 40.0 | 40.0 | 40.0 | 38.5 |
|  | PEG 400 | (parts by weight) | | | 27.0 | 27.0 | 27.0 | 27.0 | 27.0 | 27.0 | 27.0 |
|  | PEG 4000 | (parts by weight) | 25.0 | 25.0 | 12.0 | 12.0 | | 12.0 | 12.0 | 12.0 | 12.0 |
| E | Silica (Aerosil 300) | (parts by weight) | | | 5.0 | 0.2 | 15.0 | 5.0 | 5.0 | 5.0 | 5.0 |
| F | Sodium fluoride | (parts by weight) | | | | | | 1.0 | 1.0 | 1.0 | 1.0 |
| G | Na$_2$HPO$_4$ (D50: 5.2 μm) | (parts by weight) | | | | | | | | | 1.5 |
| Total | | (parts by weight) | 100.0 | 100.0 | 100.0 | 100.0 | 100.0 | 100.0 | 100.0 | 100.0 | 100.0 |
| Dentinal tubule sealing ratio (initial) | | (%) | 77.6 | 72.4 | 89.3 | 85.2 | 80.4 | 91.5 | 89.3 | 86.1 | 94.2 |
| Dentinal tubule sealing ratio (post-acid immersion) | | (%) | 57.8 | 55.4 | 76.9 | 71.5 | 68.9 | 82.3 | 76.9 | 64.8 | 85.6 |
| Decrease ratio of dentinal tubule sealing ratio | | (%) | 25.5 | 23.5 | 13.9 | 16.1 | 14.3 | 10.1 | 13.9 | 24.7 | 9.1 |
| Handling properties | | | A | A | A | A | C | A | A | A | A |
| Storage stability | | | A | A | A | A | A | A | A | A | A |
| Content of A per 100 parts by weight of total of A + B + C | (parts by weight) | | 41.3 | 41.3 | 41.3 | 41.3 | 41.3 | 41.3 | 50.0 | 50.0 | 41.3 |
| Content of B per 100 parts by weight of total of A + B + C | (parts by weight) | | 41.3 | 41.3 | 41.3 | 41.3 | 41.3 | 41.3 | 16.7 | 48.0 | 41.3 |
| Content of C per 100 parts by weight of total of A + B + C | (parts by weight) | | 17.4 | 17.4 | 17.4 | 17.4 | 17.4 | 17.4 | 33.3 | 2.0 | 17.4 |
| Content of E per 100 parts by weight of total of A + B + C | (parts by weight) | | 0 | 0 | 33.3 | 1.3 | 100.0 | 33.3 | 33.3 | 33.3 | 33.3 |
| Content of F calculated as fluorine ion content per 100 parts by weight of composition | (parts by weight) | | 0 | 0 | 0 | 0 | 0 | 0.45 | 0.45 | 0.45 | 0.45 |
| Content of G per 100 parts by weight of total of A + B + C | (parts by weight) | | 0 | 0 | 0 | 0 | 0 | 0 | 0 | 0 | 10.0 |

TABLE 4

|  |  |  | Comp. Example 1 | Comp. Example 2 | Comp. Example 3 | Comp. Example 4 | Comp. Example 5 | Comp. Example 6 |
|---|---|---|---|---|---|---|---|---|
| A | TTCP (D50: 5.2 μm) | (parts by weight) | 12.0 | 0.45 | 9.0 | 0.8 | 8.25 | 3.75 |
| B | DCPA (D50: 1.1 μm) | (parts by weight) | 1.5 | 9.3 | 0.7 | 11.2 | 6.6 | 3.0 |
| C | Calcium carbonate (D50: 2.6 μm) | (parts by weight) | 1.5 | 5.25 | 5.3 | 3.0 | 0.15 | 8.25 |
| Phosphorus-free calcium compound other than C | Calcium hydroxide | (parts by weight) |  |  |  |  |  |  |
|  | Calcium oxide | (parts by weight) |  |  |  |  |  |  |
|  | Calcium silicate | (parts by weight) |  |  |  |  |  |  |
|  | Calcium nitrate | (parts by weight) |  |  |  |  |  |  |
|  | Calcium oxalate | (parts by weight) |  |  |  |  |  |  |
| D | Glycerin | (parts by weight) | 60.0 | 60.0 | 60.0 | 60.0 | 60.0 | 60.0 |
|  | PEG 400 | (parts by weight) |  |  |  |  |  |  |
|  | PEG 4000 | (parts by weight) | 25.0 | 25.0 | 25.0 | 25.0 | 25.0 | 25.0 |
| E | Silica (Aerosil 300) | (parts by weight) |  |  |  |  |  |  |
| F | Sodium fluoride | (parts by weight) |  |  |  |  |  |  |
| G | $Na_2HPO_4$ (D50: 5.2 μm) | (parts by weight) |  |  |  |  |  |  |
|  | Water | (parts by weight) |  |  |  |  |  |  |
| Total |  | (parts by weight) | 100.0 | 100.0 | 100.0 | 99.9 | 100.0 | 100.0 |
| Dentinal tubule sealing ratio (initial) |  | (%) | 63.0 | 65.6 | 57.3 | 65.8 | 75.3 | 69.8 |
| Dentinal tubule sealing ratio (post-acid immersion) |  | (%) | 33.7 | 36.2 | 28.7 | 38.3 | 41.4 | 41.5 |
| Decrease ratio of dentinal tubule sealing ratio |  | (%) | 46.5 | 44.8 | 49.9 | 41.8 | 45.0 | 40.5 |
| Handling properties |  |  | A | A | A | A | A | A |
| Storage stability |  |  | A | A | A | A | A | A |
| Content of A per 100 parts by weight of total of A + B + C |  | (parts by weight) | 80.0 | 3.0 | 60.0 | 5.3 | 55.0 | 25.0 |
| Content of B per 100 parts by weight of total of A + B + C |  | (parts by weight) | 10.0 | 62.0 | 4.7 | 74.7 | 44.0 | 20.0 |
| Content of C per 100 parts by weight of total of A + B + C |  | (parts by weight) | 10.0 | 35.0 | 35.3 | 20.0 | 1.0 | 55.0 |
| Content of E per 100 parts by weight of total of A + B + C |  | (parts by weight) | 0 | 0 | 0 | 0 | 0 | 0 |
| Content of F calculated as fluorine ion content per 100 parts by weight of composition |  | (parts by weight) | 0 | 0 | 0 | 0 | 0 | 0 |
| Content of G per 100 parts by weight of total of A + B + C |  | (parts by weight) | 0 | 0 | 0 | 0 | 0 | 0 |

TABLE 5

|  |  |  | Comp. Example 7 | Comp. Example 8 | Comp. Example 9 | Comp. Example 10 | Comp. Example 11 | Comp. Example 12 | Comp. Example 13 |
|---|---|---|---|---|---|---|---|---|---|
| A | TTCP (D50: 5.2 μm) | (parts by weight) | 6.2 | 6.2 | 6.2 | 6.2 | 6.2 |  | 36.5 |
| B | DCPA (D50: 1.1 μm) | (parts by weight) | 6.2 | 6.2 | 6.2 | 6.2 | 6.2 | 35.0 | 13.5 |
| C | Calcium carbonate (D50: 2.6 μm) | (parts by weight) |  |  |  |  |  |  |  |
| Phosphorus-free calcium compound other than C | Calcium hydroxide | (parts by weight) | 2.6 |  |  |  |  | 0.6 |  |
|  | Calcium oxide | (parts by weight) |  | 2.6 |  |  |  |  |  |
|  | Calcium silicate | (parts by weight) |  |  | 2.6 |  |  |  |  |
|  | Calcium nitrate | (parts by weight) |  |  |  | 2.6 |  |  |  |
|  | Calcium oxalate | (parts by weight) |  |  |  |  | 2.6 |  |  |
| D | Glycerin | (parts by weight) | 60.0 | 60.0 | 60.0 | 60.0 | 60.0 | 18.0 | 11.29 |
|  | PEG 400 | (parts by weight) |  |  |  |  |  | 10.0 | 3.0 |
|  | PEG 4000 | (parts by weight) | 25.0 | 25.0 | 25.0 | 25.0 | 25.0 |  |  |
| E | Silica (Aerosil 300) | (parts by weight) |  |  |  |  |  | 4.0 | 4.0 |
| F | Sodium fluoride | (parts by weight) |  |  |  |  |  |  | 0.21 |
| G | $Na_2HPO_4$ (D50: 5.2 μm) | (parts by weight) |  |  |  |  |  | 3.0 | 5.0 |
|  | Water | (parts by weight) |  |  |  |  |  | 29.4 | 26.45 |
| Total |  | (parts by weight) | 100.0 | 100.0 | 100.0 | 100.0 | 100.0 | 100.0 | 100.0 |
| Dentinal tubule sealing ratio (initial) |  | (%) | 46.1 | 43.7 | 41.8 | 42.9 | 44.1 | 91.4 | 96.9 |

TABLE 5-continued

|  |  | Comp. Example 7 | Comp. Example 8 | Comp. Example 9 | Comp. Example 10 | Comp. Example 11 | Comp. Example 12 | Comp. Example 13 |
|---|---|---|---|---|---|---|---|---|
| Dentinal tubule sealing ratio (post-acid immersion) | (%) | 17.7 | 19.1 | 17.5 | 15.3 | 18.3 | 48.5 | 56.6 |
| Decrease ratio of dentinal tubule sealing ratio | (%) | 61.6 | 56.3 | 58.1 | 64.3 | 58.5 | 46.9 | 41.6 |
| Handling properties |  | A | A | A | A | A | A | B |
| Storage stability |  | A | A | A | A | A | D | D |
| Content of A per 100 parts by weight of total of A + B + C | (parts by weight) | 50.0 | 50.0 | 50.0 | 50.0 | 50.0 | 0 | 73.0 |
| Content of B per 100 parts by weight of total of A + B + C | (parts by weight) | 50.0 | 50.0 | 50.0 | 50.0 | 50.0 | 100.0 | 27.0 |
| Content of C per 100 parts by weight of total of A + B + C | (parts by weight) | 0 | 0 | 0 | 0 | 0 | 0 | 0 |
| Content of E per 100 parts by weight of total of A + B + C | (parts by weight) | 0 | 0 | 0 | 0 | 0 | 11.4 | 8.0 |
| Content of F calculated as fluorine ion content per 100 parts by weight of composition | (parts by weight) | 0 | 0 | 0 | 0 | 0 | 0 | 0.09 |
| Content of G per 100 parts by weight of total of A + B + C | (parts by weight) | 0 | 0 | 0 | 0 | 0 | 8.6 | 10.0 |

INDUSTRIAL APPLICABILITY

The dentinal tubule sealing material of the present invention is useful for inhibition of pain associated with dentin exposure. The dentinal tubule sealing material of the present invention can be suitably used as a tooth surface treating material, a dentifrice, a dentin hypersensitivity inhibitor, or the like.

The invention claimed is:

1. A dentinal tubule sealing material, comprising:
   tetracalcium phosphate particles;
   calcium hydrogen phosphate particles;
   calcium carbonate particles; and
   a non-aqueous dispersant,
   wherein the dentinal tubule sealing material comprises 5 to 75 parts by weight of the tetracalcium phosphate particles, 10 to 70 parts by weight of the calcium hydrogen phosphate particles, and 2 to 50 parts by weight of the calcium carbonate particles per 100 parts by weight of the total of the tetracalcium phosphate particles, the calcium hydrogen phosphate particles, and the calcium carbonate particles.

2. The dentinal tubule sealing material according to claim 1,
   wherein the tetracalcium phosphate particles have an average particle diameter of 0.5 to 10 μm,
   the calcium hydrogen phosphate particles have an average particle diameter of 0.1 to 7.5 μm, and
   the calcium carbonate particles have an average particle diameter of 0.1 to 12 μm.

3. The dentinal tubule sealing material according to claim 1, further comprising:
   silica particles, metal oxide particles, or both, having an average particle diameter of 0.002 to 0.5 μm in an amount of 0.1 to 100 parts by weight per 100 parts by weight of the total of the tetracalcium phosphate particles, the calcium hydrogen phosphate particles, and the calcium carbonate particles.

4. The dentinal tubule sealing material according to claim 1, further comprising:
   a fluorine compound in an amount calculated as fluorine ion of 0.01 to 5 parts by weight, per 100 parts by weight of the dentinal tubule sealing material.

5. The dentinal tubule sealing material according to claim 1, further comprising:
   an alkali metal phosphate in an amount of 0.5 to 15 parts by weight per 100 parts by weight of the total of the tetracalcium phosphate particles, the calcium hydrogen phosphate particles, and the calcium carbonate particles.

6. The dentinal tubule sealing material according to claim 5, wherein the alkali metal phosphate is at least one selected from the group consisting of disodium hydrogen phosphate and sodium dihydrogen phosphate.

7. The dentinal tubule sealing material according to claim 1, wherein the calcium hydrogen phosphate particles comprise particles of at least one selected from the group consisting of dibasic calcium phosphate anhydrous, monobasic calcium phosphate anhydrous, dibasic calcium phosphate dihydrate, and monobasic calcium phosphate monohydrate.

8. The dentinal tubule sealing material according to claim 1, wherein the calcium hydrogen phosphate particles comprise particles of dibasic calcium phosphate anhydrous.

9. The dentinal tubule sealing material according to claim 1, wherein the non-aqueous dispersant is at least one selected from the group consisting of glycerin, ethylene glycol, propylene glycol, diglycerin, polyethylene glycol, and polypropylene glycol.

10. The dentinal tubule sealing material according to claim 1, wherein the non-aqueous dispersant is at least one selected from the group consisting of glycerin, ethylene glycol, propylene glycol, and polyethylene glycol.

11. The dentinal tubule sealing material according to claim 1, wherein the non-aqueous dispersant is at least one of glycerin and polyethylene glycol.

12. The dentinal tubule sealing material according to claim 1, wherein the dentinal tubule sealing material comprises 10 to 60 parts by weight of the tetracalcium phosphate particles, 10 to 70 parts by weight of the calcium hydrogen phosphate particles, and 2 to 40 parts by weight of the calcium carbonate particles per 100 parts by weight of the total of the tetracalcium phosphate particles, the calcium hydrogen phosphate particles, and the calcium carbonate particles.

13. The dentinal tubule sealing material according to claim 1,
wherein the tetracalcium phosphate particles have an average particle diameter of 1.0 to 10 μm,
the calcium hydrogen phosphate particles have an average particle diameter of 0.5 to 5.0 μm, and
the calcium carbonate particles have an average particle diameter of 0.5 to 12 μm.

14. The dentinal tubule sealing material according to claim 12,
wherein the calcium hydrogen phosphate particles comprise particles of dibasic calcium phosphate anhydrous having an average particle diameter of 0.5 to 5.0 μm,
the non-aqueous dispersant is at least one of glycerin and polyethylene glycol,
the tetracalcium phosphate particles have an average particle diameter of 1.0 to 10 μm, and
the calcium carbonate particles have an average particle diameter of 0.5 to 12 μm.

15. The dentinal tubule sealing material according to claim 4, wherein the fluorine compound comprises at least one compound selected from the group consisting of sodium fluoride, potassium fluoride, ammonium fluoride, lithium fluoride, cesium fluoride, magnesium fluoride, calcium fluoride, strontium fluoride, barium fluoride, copper fluoride, zirconium fluoride, aluminum fluoride, tin fluoride, sodium monofluorophosphate, potassium monofluorophosphate, hydrofluoric acid, titanium sodium fluoride, titanium potassium fluoride, hexylamine hydrofluoride, laurylamine hydrofluoride, glycine hydrofluoride, alanine hydrofluoride, fluorosilane, and diamine silver fluoride.

16. The dentinal tubule sealing material according to claim 4, wherein the fluorine compound comprises at least one compound selected from the group consisting of sodium fluoride, sodium monofluorophosphate, and tin fluoride.

17. The dentinal tubule sealing material according to claim 5, wherein the alkali metal phosphate has an average particle diameter of 1.0 to 12 μm.

18. The dentinal tubule sealing material according to claim 1, further comprising:
silica particles having an average particle diameter of 0.002 to 0.5 μm in an amount of 0.1 to 100 parts by weight per 100 parts by weight of the total of the tetracalcium phosphate particles, the calcium hydrogen phosphate particles, and the calcium carbonate particles.

19. The dentinal tubule sealing material according to claim 1, further comprising:
silica particles having an average particle diameter of 0.002 to 0.5 μm in an amount of 0.1 to 100 parts by weight per 100 parts by weight of the total of the tetracalcium phosphate particles, the calcium hydrogen phosphate particles, and the calcium carbonate particles;
at least one of sodium fluoride, sodium monofluorophosphate, and tin fluoride, in an amount calculated as fluorine ion of 0.01 to 5 parts by weight, per 100 parts by weight of the dentinal tubule sealing material; and
at least one of disodium hydrogen phosphate and sodium dihydrogen phosphate, in an amount of 0.5 to 15 parts by weight per 100 parts by weight of the total of the tetracalcium phosphate particles, the calcium hydrogen phosphate particles, and the calcium carbonate particles.

20. The dentinal tubule sealing material according to claim 10, wherein the non-aqueous dispersant is included in an amount of 20 to 90 parts by weight per 100 parts by weight of the dentinal tubule sealing material.

* * * * *